(12) United States Patent
Ruohonen

(10) Patent No.: US 8,882,651 B2
(45) Date of Patent: Nov. 11, 2014

(54) MAGNETIC STIMULATION COILS WITH ELECTRICALLY CONDUCTING STRUCTURES

(75) Inventor: Jarmo Ruohonen, Helsinki (FI)

(73) Assignee: Nexstim Oy, Helsinki (FI)

( * ) Notice: Subject to any disclaimer, the term of this patent is extended or adjusted under 35 U.S.C. 154(b) by 472 days.

(21) Appl. No.: 13/126,765

(22) PCT Filed: Oct. 31, 2008

(86) PCT No.: PCT/FI2008/050621
§ 371 (c)(1),
(2), (4) Date: Apr. 29, 2011

(87) PCT Pub. No.: WO2010/049576
PCT Pub. Date: May 6, 2010

(65) Prior Publication Data
US 2011/0218381 A1    Sep. 8, 2011

(51) Int. Cl.
*A61N 2/02* (2006.01)
*A61N 2/00* (2006.01)
*A61B 5/05* (2006.01)

(52) U.S. Cl.
CPC . *A61B 5/05* (2013.01); *A61N 2/008* (2013.01); *A61N 2/02* (2013.01)
USPC .......................................................... 600/13

(58) Field of Classification Search
USPC ................................ 600/9–15; 128/897–899
See application file for complete search history.

(56) References Cited

U.S. PATENT DOCUMENTS

| | | | | |
|---|---|---|---|---|
| 4,791,262 A | * | 12/1988 | Ando et al. | 219/630 |
| 6,163,241 A | * | 12/2000 | Stupak et al. | 335/300 |
| 6,179,770 B1 | | 1/2001 | Mould | |
| 7,464,558 B2 | * | 12/2008 | Huang et al. | 62/51.1 |
| 2003/0050527 A1 | * | 3/2003 | Fox et al. | 600/13 |
| 2006/0004244 A1 | | 1/2006 | Phillips et al. | |

FOREIGN PATENT DOCUMENTS

| | | |
|---|---|---|
| EP | 0709115 Y | 5/1996 |
| EP | 1533625 Y | 5/2005 |
| WO | WO 2010049576 A1 | 5/2010 |

OTHER PUBLICATIONS

Pridmore et al: "A water-cooled transcranial magnetic stimulation coil" 20071203, vol. 1, No. 1, Mar. 12, 2007.

* cited by examiner

*Primary Examiner* — Catherine B Kuhlman
(74) *Attorney, Agent, or Firm* — Seppo Laine Oy; Joshua P. Wert

(57) ABSTRACT

The present invention introduces a novel apparatus (5) for providing magnetic stimuli to the human brain, the apparatus (5) comprising a casing (4) and at least one coil winding (1) adapted to carry electrical current and enclosed within the casing (4) as well as cooling means (2) situated in thermal connection with the coil (1) and comprising a body made of electrically conductive and non-magnetic material so that the mutual inductance between the coil (1) and the cooling means (2) is essentially zero.

14 Claims, 5 Drawing Sheets

MAGNETIC STIMULATION COILS WITH ELECTRICALLY CONDUCTING STRUCTURES

FIELD OF THE INVENTION

The present invention relates to stimulating biological tissue for medical purposes. In particular, the present invention relates to an apparatus for magnetic stimulation including electrically conducting structures. To be precise, the present invention relates to what is stated in the preamble portion of the independent claims.

BACKGROUND OF THE INVENTION

Biological tissue, such as the human brain, can be stimulated non-invasively when attempting to diagnose a symptom or to achieve a therapeutic effect. Using conventional techniques, it is possible to stimulate biological tissue by virtue of inducing an electric field in the tissue. The technique of magnetic stimulation accomplishes this by means of brief pulses of changing magnetic field. Various apparatuses and methods for providing biological tissue with magnetic stimulation are disclosed, e.g., in publications:
  U.S. Pat. No. 4,940,453
  U.S. Pat. No. 5,766,124
  U.S. Pat. No. 6,132,361 and
  U.S. Pat. No. 6,086,525.

Transcranial magnetic stimulation (TMS) offers a risk- and pain-free method of stimulating the human brain. For instance, stimulation of the motor cortex triggers neuronal signals that travel from the stimulated cortex to pyramidal cell fibers, and via peripheral fibers to the muscles, leading finally to the contraction of the muscles. The contraction of the muscle can be detected and its intensity measured by using an EMG device. The conduction time and the administrated stimulus intensity compared to the EMG response strength provide information that can help diagnosis of neurological diseases and trauma.

In addition to diagnostic uses, TMS has several potential therapeutic applications in diseases or disorders, such as depression, stroke and chronic pain.

In a typical TMS device, a capacitor is first charged to 1-3 kV. The maximum energy of the capacitor is normally between 300 and 500 J. The capacitor is then quickly discharged through an induction coil having small inductance of approximately 5-30 µH. The quick discharge leads into a strong brief current pulse, whose peak current can be 2-10 kA over pulse duration of 200-400 µs. In therapeutic use, magnetic impulses are administered as a sequence of pulses at different pulse repetition rates. Typically the pulse repetition rates between 0.1 and 20 Hz, but rates as high as 100 Hz have already been tested. The number of pulses fired during a treatment session is typically 2 to 5,000.

Coils suitable for above-mentioned magnetic stimulation are described in the following patent publications:
  U.S. Pat. No. 6,086,525;
  WO 0232504,
  GB 2415632,
  U.S. Pat. No. 7,367,936,
  U.S. Pat. No. 6,663,556,
  U.S. Pat. No. 6,179,770,
  GB 2261820,
  US 2008177128,
  EP 1912699, and
  U.S. Pat. No. 6,503,187.

However, conventional TMS coils feature considerable disadvantages. An essential problem is that they heat up very easily due to high current peaks at relatively high repetition rates. The heat problem causes discomfort for the patient and operator of the coil. Existing coils are resistive, typically wound from copper wire and enclosed in plastic casing. The strong current pulse with peak of several kiloamps results in ohmic losses and corresponding Joule heating in the resistive coil. At maximum pulse intensities the resistive losses are typically greater than 10 J/pulse. At a pulse rate of 10 Hz, this adds up to 100 W of heat power originating from the copper wires alone. The heat then transfers to the plastic casings and onto the patient. On the other hand, safe operation (cf. international safety standard IEC60601-1 on medical devices) of transcranial magnetic stimulation limits the maximum surface temperature of the coil to 41° C. or 106° F. To obtain maximal efficacy, the coil is manufactured out of copper wires that are as close to the head as possible, which requires the casing to be thin and the coppers close to the case surface.

The temperature of the coil and its casing depends on the heat capacities and quantities of the materials. Adding material within the coil will reduce the temperature for the same amount of heat energy. The same is achieved by using materials with high heat capacity. Heat can be absorbed into plastic casing material of the coil, or extra epoxy. However, the coil must be light and small also for usability improvement purposes, since the operator may have to handle the coil for rather long periods of time. Accordingly, adding extra weight to the device is not advantageous. Another problem with this solution is that plastic conducts heat slowly and the heat capacity of plastics is rather low compared to more progressive cooling means.

On the whole, several attempts have been made to address the heating issue by cooling the coil by circulating air or fluid substance near the source of the heat. The circulating substance can either stay within the coil or it can be lead out of the structure to exchange heat. For example, publication U.S. Pat. No. 6,179,770 discloses an arrangement of circulating air near the coil for cooling the structure of the device. Another resolution is to circulate liquids as disclosed in publication US 2006004244 and by Nielsen JF (A new high-frequency magnetic stimulator with an oil-cooled coil. J Clin Neurophysiol 1995; 12:460-467). The structure can also be cooled by absorbing heat into static liquid or solid material within the structure.

Since fluid coolants have high heat capacity, they are in principle suitable for cooling purposes. In particular, water has superior volumetric heat capacity, i.e. Joules absorbed per volume. However, the use of liquid coolants makes the device considerably complex and creates a risk of spilling the coolant on the patient in the event of a broken coil casing. Another problem with liquids is that they conduct heat relatively poorly from the coil to its surroundings. Air-cooling is not preferred either, because of increased complexity and also excess noise emanating from the necessary cooling blowers.

Metals would be suitable materials for conducting heat away from the coil because they have high heat conductivity, i.e. they are able transfer heat quickly from one place to another. However, metals have not been used in close proximity of TMS coils, because the changing magnetic field of the coil induces eddy currents in metals that will heat them up. There will also be a force between the primary current in the TMS coil and the eddy current. The force can create a considerable risk and break the construction. The force also causes loud audible noise pulses, which are harmful for occupants of the operating room.

Currently there are no known coil solutions featuring electrically conducting non-ferromagnetic material in the immediate vicinity of the coil coppers. Ferromagnetic materials have, however, been used for the purpose of providing a magnetic core to improve efficiency of the induction coil as is disclosed in publications WO 91/04071 and WO 2007/016279.

SUMMARY OF THE INVENTION

The present invention is based on magnetic stimulator apparatus comprising a casing and at least one induction coil winding adapted to carry electrical current enclosed therein. Adjacent to the induction coil windings and within the casing is fitted means for cooling the coil windings and their surroundings, which means comprises a body made of electrically conductive and non-magnetic material and which is designed so that the mutual inductance between the coil and the cooling means is essentially zero. The invention enables the use of electrically conductive materials near the induction coil windings without compromising the safety and functionality of the device. To be precise, the invention is characterized by what is stated in the characterizing portion of the independent claim 1.

Considerable advantages are gained with the aid of the invention. The possibility to use metals near the coil windings offers new opportunities for transferring heat dissipated in the stimulator coil efficiently away from the coil windings. This leads to lower peak temperature on the surface of the coil casing, which is to be placed in contact with the patient's head, improving user comfort significantly. Moreover, the use of metals near the coil windings can offer improved rigidity in the coil structures.

According to one embodiment of the invention, further advantages can be gained by having a cooling structure without circulating heat transfer fluid and the necessary auxiliary components, such as blower fans causing excess noise. This way the structure of the device becomes more robust and reliable as well as lighter, which is beneficial in terms of operator ergonomics. The simpler construction is also inexpensive and quick to manufacture due to minimized variety of parts. In addition, since there is no heat transfer fluid involved, there is no risk of spillage or seepage of cooling liquid onto the patient, nor is there a need for liquid change, which has an improving effect on maintenance intervals.

According to another embodiment of the invention, the device may have parts of the casing made of electrically conducting and non-magnetic material, such as metals like copper or silver and plastics or ceramics. There is therefore an additional advantage of precise and accurate manufacturing of the product as well as being able to construct a rigid structure supported by the metallic elements.

BRIEF DESCRIPTION OF THE DRAWINGS

In the following the present invention is described in greater detail with references to the accompanying drawings, in which.

DESCRIPTION OF EXEMPLARY EMBODIMENTS

Figure 1:
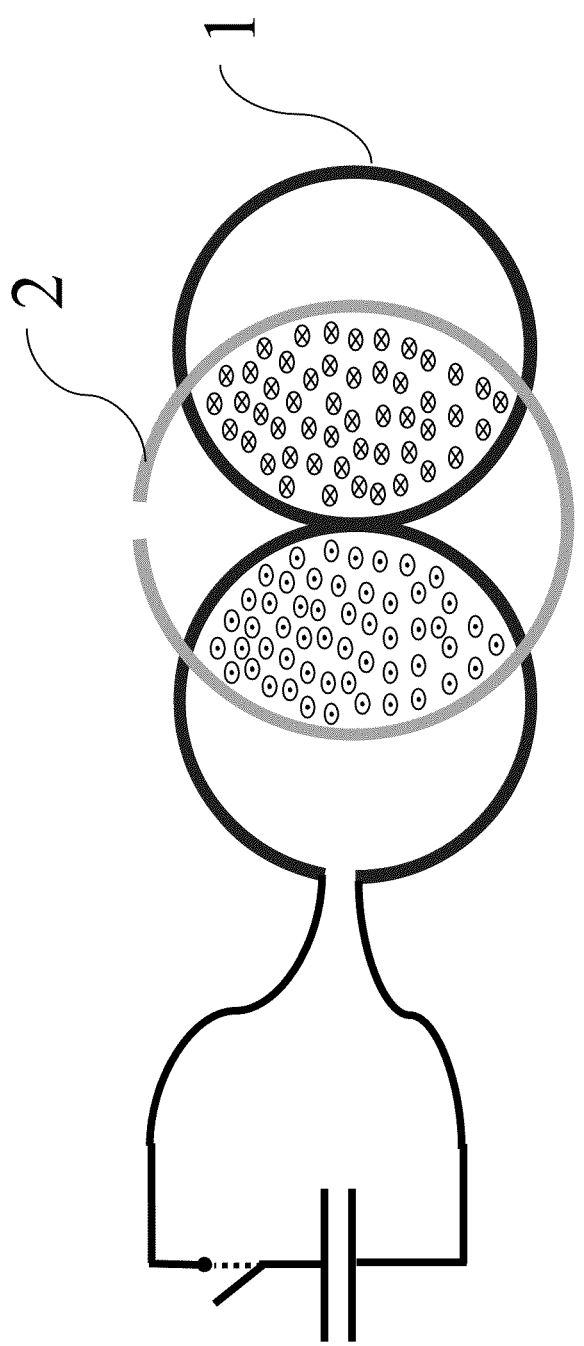
FIG. 1 shows a symmetric bow shaped coil and a cooling element between the two loops.

According to the present invention, it is possible to provide a magnetic stimulator coil with metallic cooling elements. The cooling constructions are chosen so that the copper windings of the TMS coil have minimal electromagnetic coupling with the electrically conducting cooling and supporting structures. This is achieved when the mutual inductance between the coil and the electrically conducting supporting/cooling piece/pieces is zero or close to zero.

In principle, the cooling structure can be manufactured of any electrically conducting and non-magnetic material having good thermal properties, i.e., its coefficient of thermal conductivity is high, preferably greater than $10\ \text{WK}^{-1}\text{m}^{-1}$, or its heat capacity is high, preferably greater than $1\ \text{Jcm}^{-3}\text{K}^{-1}$, or both. Therefore suitable materials for herein described applications include for example copper and silver. By electrically conducting material is meant a material having the electrical conductivity of at least 0.01 MS/m, preferably at least 30 MS/m. By non-magnetic material is meant materials that have relative permeability close of 1-10. Such materials include, for example, copper and aluminium. The cooling structure may also contain small pieces of conducting material enclosed in non-conducting material. The material does not have to be metal, but can also be derived from polymers or ceramics whose characteristics are within the limits listed above. When the structure is used as support structure instead of cooling, e.g., to provide a more robust design, it is not required thermal conductivity of the material is not important. As described, the stimulator device is designed so that the mutual inductance between the stimulating copper coil and the metallic cooling and support structures is essentially zero. In this context, by essentially zero is meant a mutual inductance between the two elements that is not greater than about 1 µH. The basic idea behind the design is that the magnetic field induced by the electrical current in the TMS coil does not flow through or pass by the cooling structure so that there would occur a significant eddy current in the cooling structure. This is achieved by having the cooling structure located so that the net magnetic flux through the structure is zero or close to zero. This is the same as saying that the mutual coupling, or inductance between the objects is small.

Mathematically this can be expressed as follows. The stimulating coil induces an electromotive force emf in the cooling/support structure equal to:

$$\text{emf} = -d\Phi/dt, = MdI/dt,$$

where $\Phi$ is the magnetic flux through the cooling/support structure, M is the mutual inductance and I is the current in the induction coil.

The mutual inductance can be expressed by the Neumann formula:

$$M_{ij} = \frac{\mu_0}{4\pi} \oint_{C_i} \oint_{C_j} \frac{ds_i \cdot ds_j}{|R_{ij}|}$$

where i denotes the inductance coil and j the support/cooling structure. The coil windings are along the path $C_i$ and $ds_i$ is a unit vector along the path. The path of the cooling/support structure is defined by $C_j$ and $ds_j$ is a unit vector along the path. The paths are closed paths.

Modern engineering design software typically feature modelling tools, which are capable of calculating mutual coupling between objects. Accordingly, designs utilizing the described principle include, for example, a tube-like cooling structure located so that the magnetic fields of two coils penetrate mostly the jacket of the cooling structure. More importantly, the magnetic field generated by the loop on the left is of different direction than that of the right loop. Therefore electric currents within the cooling element induced by the two magnetic fields cancel each other out.

Such a design is illustrated in FIG. 1. In this particular embodiment there is provided a TMS device 5 having a symmetric bow shaped, i.e. number "eight" shaped, TMS coil 1 adapted to carry electrical current and equipped with a circular cooling structure 2, which may also be referred to as cooling means 2. The cooling structure 2 can also have a closed shape other than a circle. The cooling structure 2 is located so that its centre is aligned with the node of the two loops of the symmetric bow shaped coil 1. In addition, the diameter of the cooling structure 2 is approximately the same as of the loops of coil 1. According to this design, there are two opposite magnetic fields within the cooling structure 2. On the left, the field is upward from the figure illustrated with a circle having a dot in the middle, which represents the tip of an arrow pointing upward from the plane. On the right, the field is vice versa downward from the plane of the figure illustrated with a circle having a cross in the middle, which represents the tail of an arrow pointing downward from the plane. Therefore, the electric current in the cooling structure 2 induced by the two magnetic fields of the coil 1 cancel each other out resulting in zero mutual inductance. Because the cooling structure is in the immediate vicinity of the coil 1, heat is transferred through the casing into the cooling structure 2.

Figure 2:
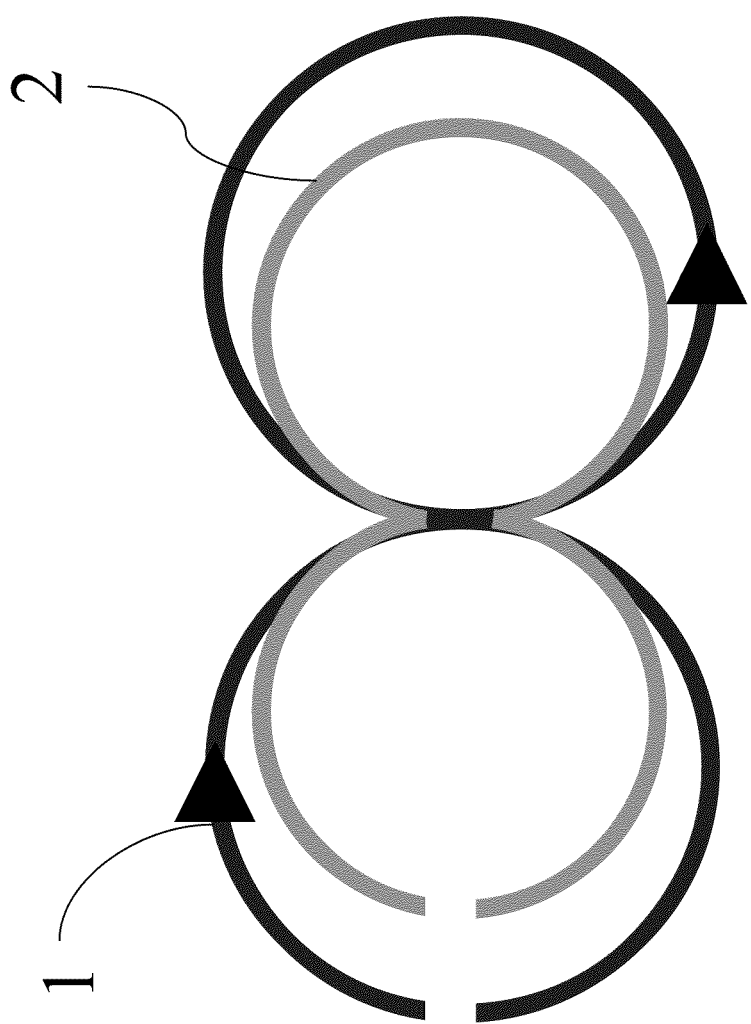
FIG. 2 shows a symmetric bow shaped coil housing two cooling elements.
Figure 5:
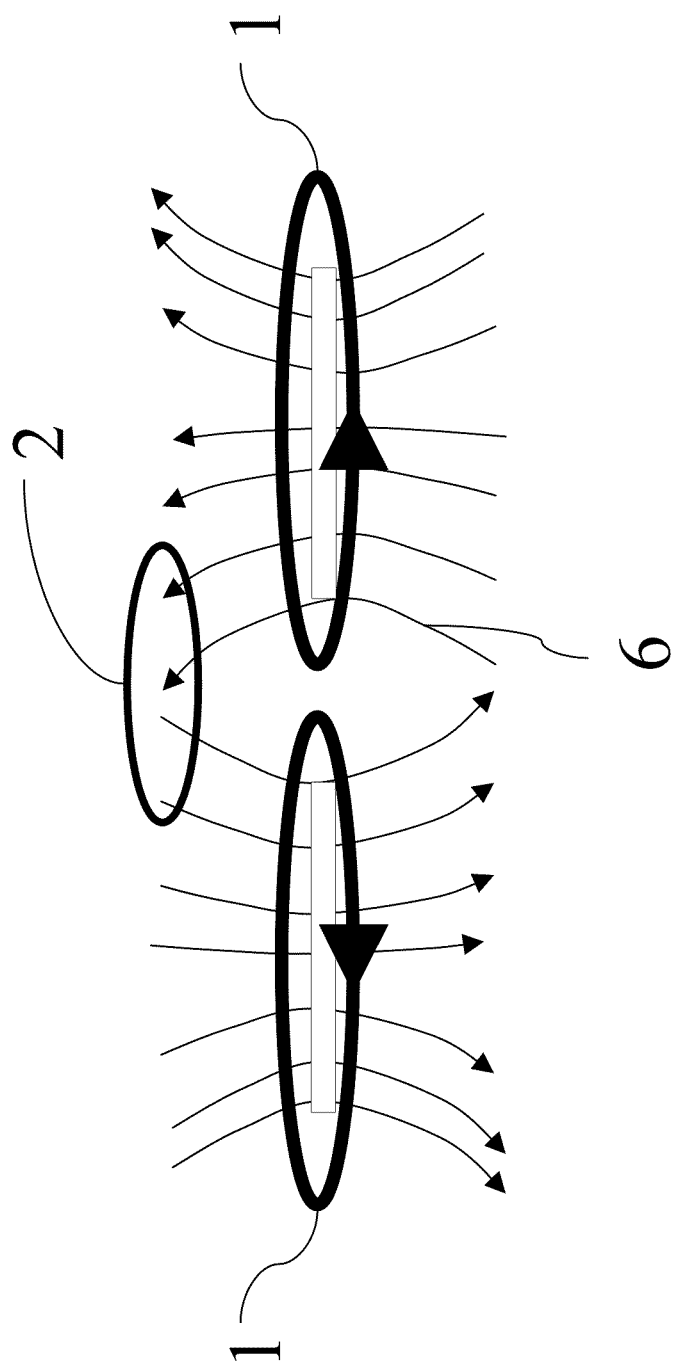
FIG. 5 shows a symmetric bow shaped coil and a circular cooling element.

According to another embodiment of the invention and as illustrated in FIG. 2, a TMS device 5 comprises a symmetric bow shaped TMS coil 1 adapted to carry electrical current and equipped with a cooling or support structure 2. The left- and right-hand side loops of the coil I are in opposite direction in figure-8 configuration. The cooling structure 2 is constructed so that the left- and the right-hand side loops of the coil 1 induce into the cooling structure 2 exactly opposite direction currents so that the net current is zero. The cooling structures 2 are fitted within the loops of the TMS coil 1 so that, although not being coaxial, the loops share their node with that of the coil 1. As a result, the magnetic fields generated by the coil 1 pass through the cooling structures 2 in a way that induces practically no electric current. This phenomenon is further presented in FIG. 5, wherein a cooling or support structure 2 has closed path, but the flux through the surface spanned by the path is zero. Zero flux is achieved by placing the structure 2 symmetrically so that the integrated flux from each half of the stimulating coil is equal but in opposite direction.

It is also possible to have different cooling and support structure designs featuring a similar zero magnetic coupling as the examples described above. As said, modern engineering design software feature modelling aids to produce such designs. However, as part of the design process, extensive attention should be paid to verify that the mutual inductivity is indeed zero for guaranteeing the safety of the patient and operator. The verification can be performed in at least three simple ways. First, with a precision inductance meter, the coil inductance is measured when the electrically conducting piece is present and again when it is distant. A bigger change in the inductance of the measured coils indicates more coupling. Second, TMS pulses are fired through the coil and any changes in the pulse shape and duration are measured through the coil when the electrical conductor is in place. Third, TMS pulses fired and forces dislocating the electrically conducting parts are observed.

Figure 3:
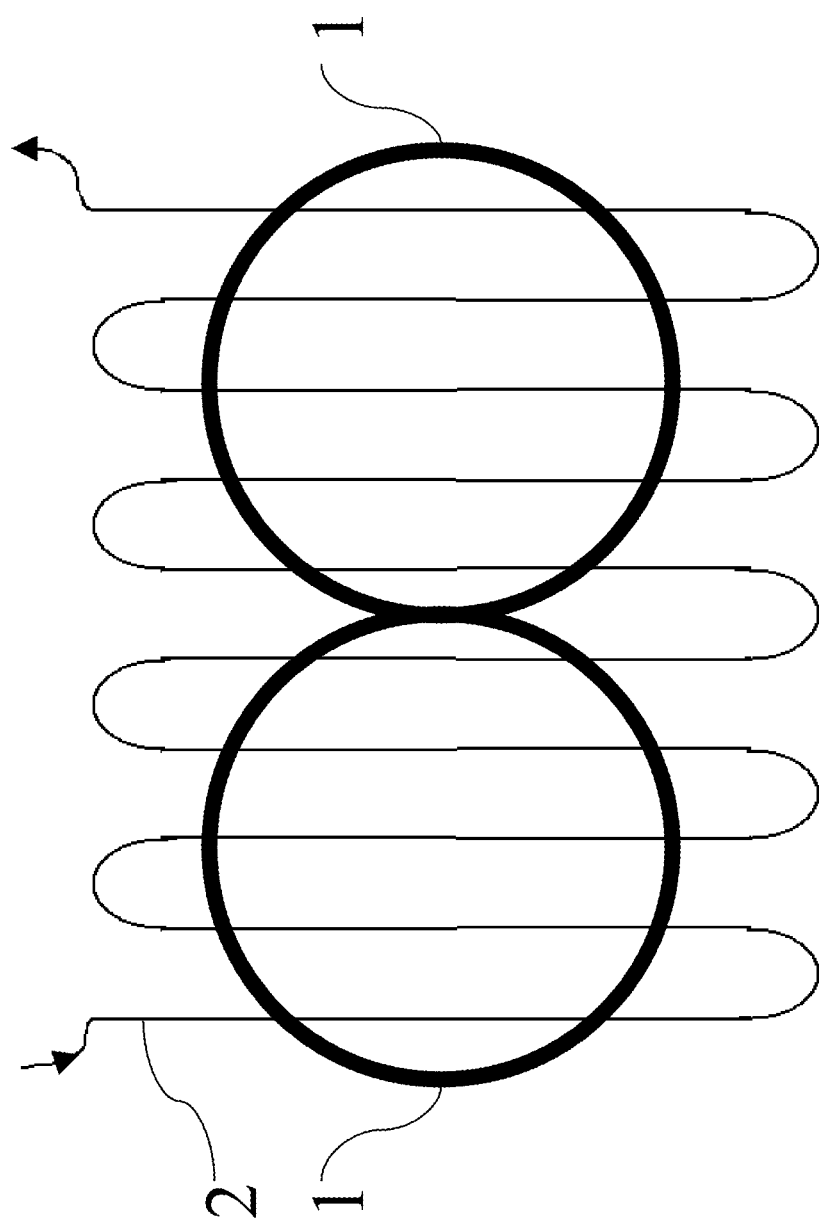
FIG. 3 shows a cross-section view of a stimulator with two stimulating coils and a tube-like cooling structure.

As it is possible to design a cooling structure 2 made of electrically conducting material, it is also possible to choose from various methods of utilizing the benefits of thermal properties of such materials. For instance, a cooling structure 2 could be used for simply storing the heat conducting to the cooling structure from the warm or hot coil 1. Another embodiment would be to gain advantage from its high coefficient of thermal conductivity by using the structure 1 to conduct the heat away from the TMS device 5. This could be done passively by having simple cable leading the heat out. Alternatively by active cooling, the cooling structure 2 could comprise a tube of electrically conducting material bent to form a heat exchanger as illustrated in FIG. 3. According to this embodiment of the invention, the cooling structure 2 is made from a hollow pipe that has been shaped to have a plurality of vertical portions and curves connecting them. The structure has to open ends, from one of which heat transfer fluid, i.e. coolant, is fed into the system and from the other it is lead out. The coolant is then preferably lead to another heat exchanger in which the coolant is then cooled. As the coolant circulates in the system, it absorbs heat from the TMS coil I or coils 1 and transfers it outside of the device where it is cooled in another heat exchanger. The heat transfer fluid can be any sort of a suitable cooling liquid, such as water, ethylene glycol, diethylene glycol, propylene glycol, or a gas, such as air. The jacket of the tube itself would also transfer some heat from the vicinity of the coil 1. Since such a design requires a rather complex construction due to coolant circulation, the cooling structure 2 can alternatively be made of solid wire, which would transfer the heat itself without a coolant. This sort of an arrangement would be suitable for applications generating only small amounts of heat and not requiring powerful cooling.

Figure 4:
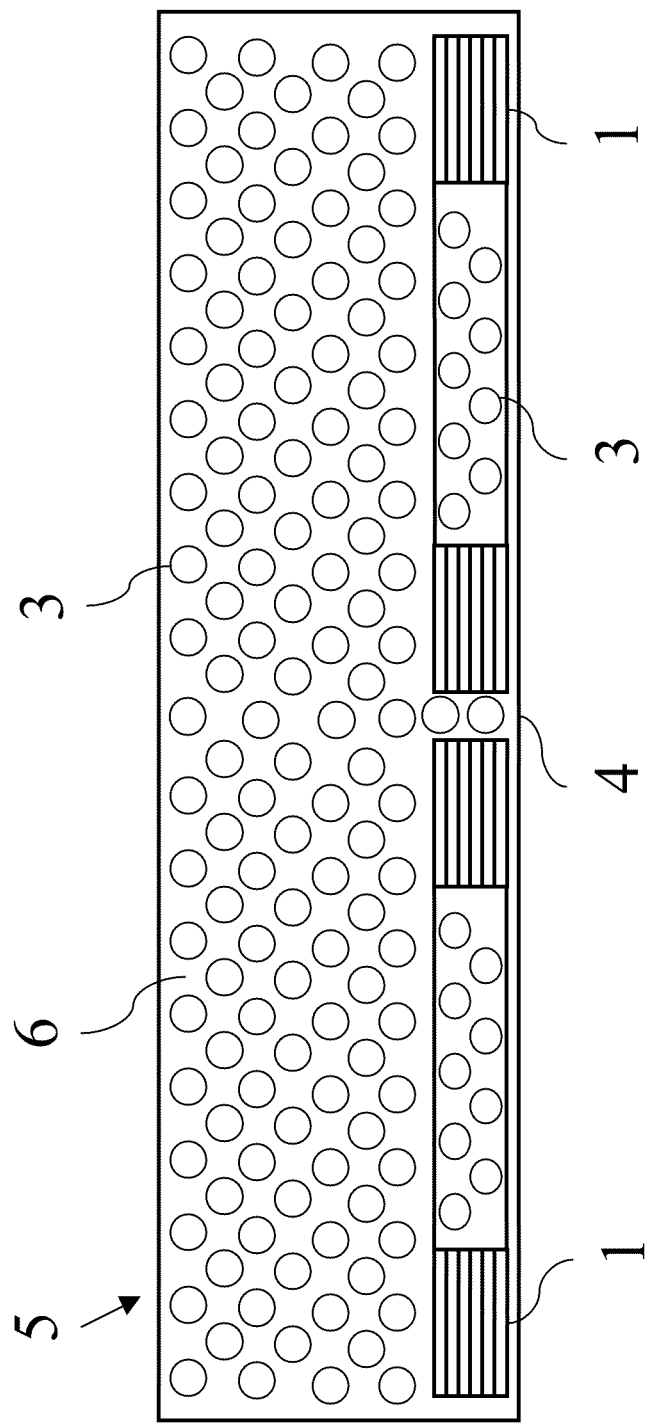
FIG. 4 shows a cross-section view of a stimulator with two stimulating coils and a bead-like cooling structure.

As said, the electrically conducting cooling element 2 can also be employed merely to store the heat generated by the TMS coil 1 within the TMS device 5 instead of conducting it onto the patient through the engaging face of the device 5. As illustrated in FIG. 4 and according to one embodiment of the invention, the TMS device 5 is equipped with small pellets 3 that absorb the heat energy of the coils 1 and store it so that only minimal heat is conducted to the engaging face 4 of the device 5. As the pellets 3 as arranged so that there is high electrical resistance between adjacent pellets, and that the eddy currents induced in them by the TMS coil is minimal. To be more precise, the volume resistivity is preferably limited to above 100 Ohm·cm, and so that the mutual inductance between the coil and the cooling means is essentially zero, i.e. below 1 µH. The size of each pellet should therefore be practically less than 1 mm, and each pellet should have an insulating surface. The material of the pellets can be chosen from those described above. Pellets can fill the space around the coil's copper windings inside the coil covers. The pellets can also be fitted into a supporting material, i.e. a binding filling 6, such as epoxy, which also provides additional insulation between the metallic pieces.

Having metallic structures with zero electrical coupling with the TMS coil windings 1 is beneficial also in terms of the construction of the TMS coil 5 itself. According to one embodiment of the invention, construction elements of the TMS coil 5 can also made from metallic and non-magnetic material providing that the mutual inductance between the construction element and the TMS coil 1 is essentially zero. Traditionally the TMS coils 5 are made of plastics, in particular epoxy and POM or similar. Unfortunately plastic materials are typically not as stiff as metals and they are less precise to manufacture than metal structures. Since the coil 1 is preferably constructed to be as robust as possible with its wires precisely positioned with respect to the coil casing, it is advantageous to use metallic materials as a construction material to improve the stiffness and manufacturing accuracy of the device. It is therefore possible to enhance the mechanical properties of the TMS coil 5 by using metallic construction elements that have essentially zero magnetic coupling with the coil 1. Such construction can be used to manufacture coils that resist more pulses before breaking and hence have longer lifetime.

Generally speaking, it is essential that, regardless of the cooling element arrangement, the cooling structure 2 is in thermal connection with the coil 1. In this context, thermal connection means that the two elements are arranged in such vicinity of each other that a temperature change of 1° C. in the coil 1 changes the temperature of the neighbouring parts of the cooling structure 2 by at least 0.05° C., preferably at least 0.1° C. When expressed this way, the exact quantity of the thermal connections, however, depends for instance on the mass of the coil and the cooling element. When the structure is used for the purpose of support structure, and not cooling, thermal connection is irrelevant.

On the basis of the examples described above, it is obvious that within the scope of the invention, numerous solutions differing from the embodiments described above can be implemented. Thus the invention is not intended to be restricted to apply to only the examples described above, but instead the patent protection should be examined to the full extent of the accompanying claims.

LIST OF REFERENCE NUMBERS

| Ref. No. | Part |
| --- | --- |
| 1 | TMS coil |
| 2 | Cooling element |
| 3 | Electrically conducting pellet |
| 4 | Engaging face (to the patient) of the TMS coil |
| 5 | TMS coil |
| 6 | Filling |

The invention claimed is:

1. An apparatus for providing magnetic stimuli to the brain comprising:
a casing,
at least one coil winding adapted to carry an electrical current and enclosed within the casing,
a cooling structure having a body made of electrically conductive and non-magnetic material in thermal connection with the coil,
wherein the cooling structure is arranged in relation to the at least one coil winding such that the mutual inductance between the coil and the cooling structure is essentially zero,
wherein the at least one coil winding is a symmetric bow shaped coil winding, and
wherein the cooling structure is a closed shape with its center aligned with a node of two loops of the symmetric bow shaped coil winding.

2. An apparatus according to claim 1, wherein the electrically conductive and non-magnetic material of the cooling means is adapted to absorb heat.

3. An apparatus according to claim 1, wherein the electrically conductive and non-magnetic material of the cooling means is adapted to conduct heat.

4. An apparatus according to claim 1, wherein the cooling means is adapted to form pathways for a heat transfer fluid.

5. An apparatus according to claim 4, wherein the heat transfer fluid is a liquid including at least ethylene glycol, diethylene glycol, propylene glycol or water.

6. An apparatus according to claim 4, wherein the heat transfer fluid is gas.

7. An apparatus according to claim 1, wherein the electrically conductive and non-magnetic material is copper.

8. An apparatus according to claim 1, wherein the electrically conductive and non-magnetic material is aluminium.

9. An apparatus according to claim 1, wherein the electrically conductive and non-magnetic material is silver.

10. An apparatus according to claim 1, wherein the cooling means comprises small pieces of conducting material with isolated surfaces such that the electrical conductivity between the pieces is essentially zero.

11. An apparatus according to claim 10, wherein the pieces are separated and binded by a filling made of an isolating material selected from the group of epoxys, plastics or ceramics.

12. An apparatus according to claim 1,
wherein the casing comprises a construction structure of electrically conducting and non-magnetic material, and the mutual inductance between the structure and the coil is essentially zero.

13. An apparatus according to claim 1, wherein the cooling structure is circular.

14. An apparatus according to claim 1, wherein the cooling structure is a closed shape.

* * * * *